US00PP17298P2

(12) United States Plant Patent
Korlipara

(10) Patent No.: US PP17,298 P2
(45) Date of Patent: Dec. 19, 2006

(54) ***ECHINACEA PURPUREA* PLANT NAMED 'SPARKLER'**

(50) Latin Name: *Echinacea purpurea*
Varietal Denomination: Sparkler

(75) Inventor: Harini Korlipara, Canby, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 11/225,929

(22) Filed: Sep. 13, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct cultivar of *Echinacea purpurea* plant named 'Sparkler' characterized by its distinctive leaves with mottled variegation.

1 Drawing Sheet

Botanical denomination: *Echinacea purpurea.*
Variety designation: 'Sparkler'.

The present invention relates to a new and distinct cultivar of *Echinacea purpurea* and given the cultivar name 'Sparkler'. *Echinacea* is in the family Asteraceae. This new cultivar originated as a whole plant mutation in tissue culture of *Echinacea purpurea* 'Ruby Giant' (an unpatented plant) in Canby, Oreg.

To the breeder's knowledge, this new cultivar is unique. It is the only known variegated *Echinacea purpurea* that is commercially available.

This new *Echinacea purpurea* cultivar is distinguished by:

1. Mottled leaf variegation.
2. Semi dwarf habit.
3. Lovely fragrance.
4. Rose pink "flowers" with orange centers.
5. Good vigor.

This new cultivar has been reproduced only by asexual propagation (division and tissue culture). Each of the progeny exhibits identical characteristics to the original plant. Asexual propagation by division and tissue culture using standard micropropagation techniques with lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
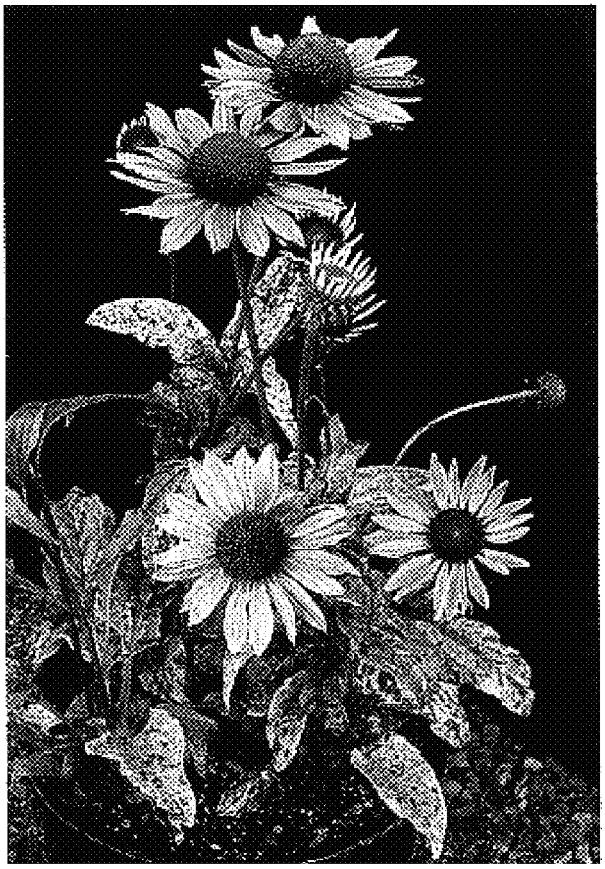
FIG. 1 shows a one year old *Echinacea purpurea* 'Sparkler' growing in a 3-gallon pot in the greenhouse in the August in Canby, Oreg.
Figure 2:
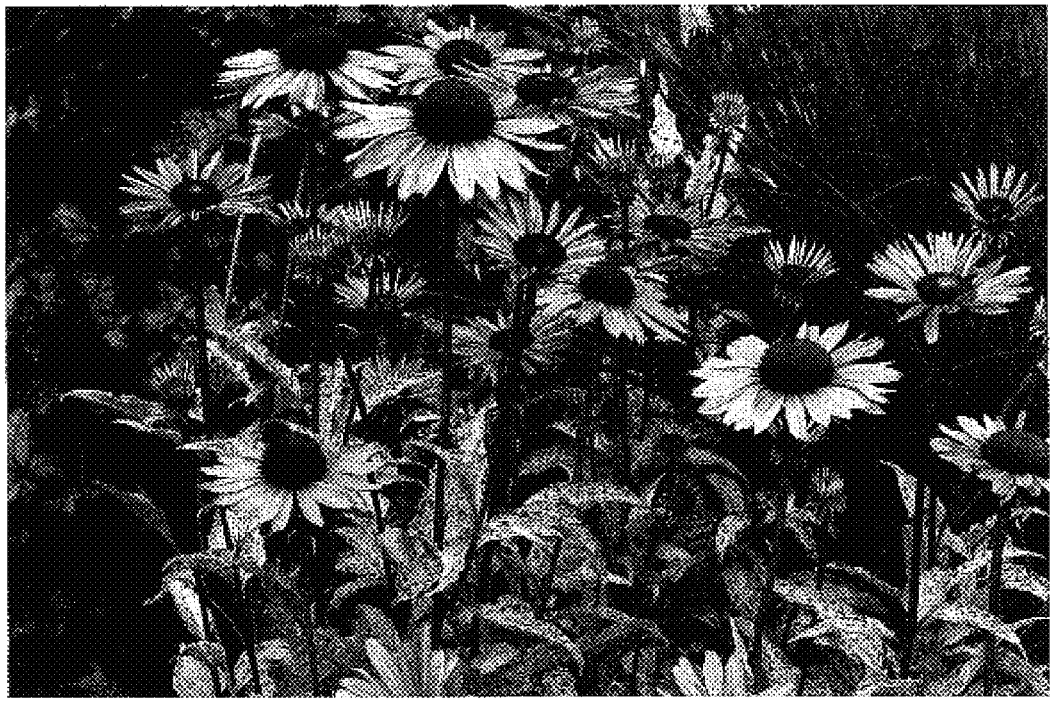
FIG. 2 shows a one year old planting growing in the ground in full sun in the show gardens.

The following is a detailed description of the new *Echinacea purpurea* cultivar based on observations of a one-year-old specimen growing in a one-gallon pot in the greenhouse in Canby, Oreg. The color descriptions are all based on The Royal Horticultural Society Colour Chart.

Plant:

*Type.*—Herbaceous perennial.
*Hardiness.*—USDA Zones 4 to 9.
*Size.*—18 cm wide and 16 cm. tall to top of basal foliage.
*Form.*—Basal clump.
*Vigor.*—Excellent.
*Roots.*—Fibrous, with many downward growing and few laterals, ivory in color, Yellow White 158D. Roots develop easily from cuttings from the crown.

Leaf:

*Type.*—Simple.
*Shape.*—Lanceolate to ovate basal leaves, lanceolate cauline leaves.
*Arrangement.*—Alternate.
*Blade length.*—11 to 15.7 cm. on basal leaves and 5.5 to 11 cm on cauline leaves.
*Blade width.*—5.5 to 6.5 cm on basal leaves and 2 to 3 cm on cauline leaves at the widest part.
*Margins.*—Slightly undulate and broadly crenate.
*Apex.*—Acuminate.
*Base.*—Attenuate.
*Texture.*—Like sandpaper.
*Surface texture.*—Strigose.
*Venation.*—Pinnate.
*Color.*—Topside — Patchy and speckled or mottled variegation of cream, Yellow 4D, with deep green, between Green 139A and Yellow Green 147A on the darkest patches, and lighter green, Yellow Green 147A on other patches. Bottom — Yellow Green 147B to C speckled with cream, Yellow 4D.
*Petiole length.*—7 to 8 cm if basal leaf, 0 to 4 cm if cauline leaf.
*Petiole surface texture.*—Strigose.
*Petiole color.*—Yellow Green 146C with Greyed Purple 187A at base of basal leaves.

Inflorescence:

*Type.*—Long stalked terminal heads.

*Number of heads per plant.*—3 to 5 in first flush.

*Peduncle.*—Height: 47 cm. Diameter: 0.5 cm. near "flower" head. Strength: excellent. Surface texture: strigose. Color: Yellow Green 146B with darkish linear shaped spots of Brown 200B.

Flowering bud: Cylindrical, 3 cm wide and 2 cm deep, disc area flat and Yellow Green 144A, immature ray florets are Yellow Green 149D with tips Yellow Green 144A.

Ray and disc florets:

*Type.*—Perfect, zygomorphic in composite head.

*Size.*—10 cm. wide and 3.5 cm deep as disc enlarges.

*Ray florets.*—Usually 24, sometimes twisted, no pistil or stamen. Count: average 40 ray florets per inflorescence. Shape: Oblong with the tip 2 toothed and a clawed base. Length: 3.5 to 4.7 cm long. Width: 1.1 cm. Texture — satiny, soft. Surface texture— glabrous except for bottom side where sparsely strigose.

*Disc.*—Shape — convex becoming conic.

*Size.*—2 to 3.7 cm wide and becoming 3.5 cm deep with maturity.

*Count.*—Approximately 280 disc floret per inflorescence.

*Individual disc florets.*—1 cm long, Yellow Green 146D, 5 lobed, each floret with one persistent, very stiff bract, 1.2 cm long, which gives the green to orange disc color. Bract color Orange 26A with a red tip, Greyed Purple 185A.

*Pistil.*—1 per disc floret, 6 mm long; ovary White 155D and 2 mm long, 1 mm wide; style 3 mm long White 155A; stigma extruding, 2-branched, Greyed Purple 187A.

*Stamen.*—5 per disc floret, filaments 3.5 mm long and 0.25 mm wide, anthers flat and oblong shaped, 2.5 mm long and 0.5 mm wide, pollen color cream, Yellow 9D.

*Color.*—Ray florets, topside — Red Purple 68B. Ray florets, bottom side — Red Purple 65A. Disc florets overall — Yellow Green 146A before opening and Orange 26C when disc florets are mature.

*Phyllaries.*—In five to six leafy series, lobes lanceolate in shape, reflexed, strigose, 2 mm wide and 3 to 9 mm long, Yellow Green 147B.

*Bloom period.*—July through September in Canby, Oreg.

*Lastingness.*—Each inflorescence lasts for two to three weeks.

*Fragrance.*—Lovely.

Fruit and seed: None.

*Fertility.*—Sterile.

Disease and pests: *Echinacea* are suscetible to leaf miners, powdery mildew, bacterial spots, and gray mold. None of these have been observed on plants grown under commercial conditions in Canby, Oreg.

COMPARISONS TO SIMILAR *ECHINACEA*

Compared to *Echinacea purpurea* 'Ruby Giant', an unpatented plant and the parent, the new cultivar is shorter with mottled variegation on leaves. The ray florets of the new cultivar are a lighter red purple in color.

Compared to *Echinacea purpurea* 'Prairie Frost', an unpatented plant, the new cultivar has mottled leaf variegation rather than edged variegation.

I claim:

1. A new and distinct *Echinacea purpurea* plant, as herein shown and described.

* * * * *